(12) United States Patent
Du et al.

(10) Patent No.: US 10,781,173 B2
(45) Date of Patent: Sep. 22, 2020

(54) METHOD FOR PREPARING APREMILAST

(71) Applicant: ZHEJIANG HUAHAI PHARMACEUTICAL CO., LTD, Linhai, Zhejiang (CN)

(72) Inventors: Xiaoqiu Du, Zhejiang (CN); Lianchao Zhou, Zhejiang (CN); Jiegen Liu, Zhejiang (CN)

(73) Assignee: ZHEJIANG HUAHAI PHARMACEUTICAL CO., LTD, Linhai, Zhejiang (CN)

( * ) Notice: Subject to any disclaimer, the term of this patent is extended or adjusted under 35 U.S.C. 154(b) by 38 days.

(21) Appl. No.: 16/313,732

(22) PCT Filed: Jun. 30, 2017

(86) PCT No.: PCT/CN2017/091046
§ 371 (c)(1),
(2) Date: Feb. 25, 2019

(87) PCT Pub. No.: WO2018/001353
PCT Pub. Date: Jan. 4, 2018

(65) Prior Publication Data
US 2019/0248740 A1    Aug. 15, 2019

(30) Foreign Application Priority Data
Jun. 30, 2016   (CN) .......................... 2016 1 0528570

(51) Int. Cl.
| C07D 209/48 | (2006.01) |
| C07D 209/46 | (2006.01) |
| C07C 45/63 | (2006.01) |
| C07C 317/28 | (2006.01) |
| C07C 315/04 | (2006.01) |
| C07C 49/84 | (2006.01) |

(52) U.S. Cl.
CPC ............ C07D 209/48 (2013.01); C07C 45/63 (2013.01); C07C 49/84 (2013.01); C07C 315/04 (2013.01); C07C 317/28 (2013.01); C07D 209/46 (2013.01)

(58) Field of Classification Search
CPC ................................................... C07D 209/48
See application file for complete search history.

(56) References Cited

U.S. PATENT DOCUMENTS

2014/0081032 A1    3/2014   Connolly

FOREIGN PATENT DOCUMENTS

| CN | 101683334 A | 3/2010 |
| CN | 104478790 A | 4/2015 |
| CN | 105218428 A | 1/2016 |
| CN | 105330586 A | 2/2016 |

OTHER PUBLICATIONS

English translation of International Search Report for International Application No. PCT/CN2017/091046, dated Sep. 27, 2017, 2 pages.

Primary Examiner — Golam M Shameem
(74) Attorney, Agent, or Firm — Armstrong Teasdale LLP

(57) ABSTRACT

Provided is a method for preparing apremilast of formula I. Method one: (S)-1-(3-ethoxy-4-methoxyphenyl)-2-(methylsulfonyl)ethylamine N-acetyl-L-leucine salt of formula II is reacted with 3-acetylaminophthalic anhydride of formula III in an aprotic solvent to produce the compound of formula I; method two: (S)-1-(3-ethoxy-4-methoxyphenyl)-2-(methylsulfonyl)ethylamine N-acetyl-L-leucine salt of formula II is reacted with 3-acetylaminophthalic anhydride of formula III in an organic solvent in the presence of an organic alkali or an alkali metal hydride to produce the compound of formula I. The method for preparing apremilast requires inexpensive raw materials and reagents, is suitable for industrial production, and has great economic effects.

13 Claims, No Drawings

METHOD FOR PREPARING APREMILAST

This application claims priority to International Patent Application No. PCT/CN2017/091046, filed on Jun. 30, 2017, which claims priority to CN Patent Application No. CN201610528570.7, filed on Jun. 30, 2016, the disclosures of which are hereby expressly incorporated by reference in their entireties.

TECHNICAL FIELD

The present invention belongs to the field of medicine and chemical industry, and particularly relates to a method for preparing apremilast.

TECHNICAL BACKGROUND

Apremilast is a PDE4 inhibitor developed by Celgene, and many indications such as rheumatoid arthritis, psoriatic arthritis, Behcet's disease, ulcerative colitis are currently developed clinically. On Mar. 21, 2014, the FDA approved the first indication-adult active psoriatic arthritis (PsA). Trade Name: OTEZLA® (according to a post-marketing requirement of FDA, the manufacturer will evaluate the exposure effects of the drug on pregnant women through a registered study about pregnancy). Three clinical trials evaluated the safety and efficacy of apremilast in the treatment of PsA. The ACR20 response rates of the apremilast group and the placebo group were 32-41% and 18-19%, respectively.

As an oral antirheumatic drug with a new mechanism of action, apremilast is different from the commonly used anti-TNF monoclonal antibodies in clinical practice. Thomson Pharma predicted that the sale of apremilast would be $1.219 billion in 2018, $516 million in 2015, and the sale would grow rapidly. The sale of apremilast is expected to reach a maximum of $2 billion. Compared with the same kind of drugs, apremilast has the following advantages: it can inhibit the formation of various pro-inflammatory mediators (PDE-4, TNF-α, IL-2, interferon γ, leukotrienes, NO synthase) and exert anti-inflammatory action; in addition to be approved for psoriatic arthritis, phosphodiesterase 4 (PDE4) selective inhibitor is approved by the FDA in September 2014 for patients subjected to phototherapy or systemic therapy for moderate or severe treatment of plaque psoriasis, and it is the first and only PDE4 inhibitor approved for the treatment of plaque psoriasis; clinical trials have shown that OTEZLA can reduce erythema, thickening and scaling in patients with moderate or severe plaque psoriasis; clinical trials have proven that apremilast is well tolerated and has fewer adverse effects. In the clinical trials, compared with the placebo group, patients of the Otezla treatment group showed improvements in PsA signs and symptoms, including tenderness, joint swelling and physical function.

Patent CN 101683334A reports the preparation of apremilast (1) from (S)-1-(3-ethoxy-4-methoxyphenyl)-2-(methylsulfonyl)ethylamine N-acetyl-L-leucine salt (2) and 3-acetylaminophthalic anhydride (3) using acetic acid as a solvent, the synthesis route is as follows:

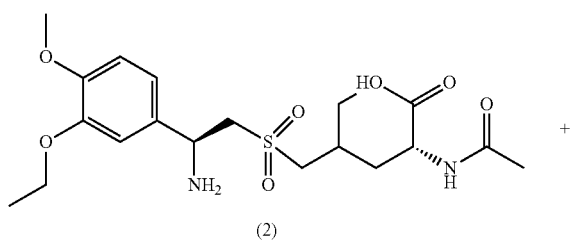

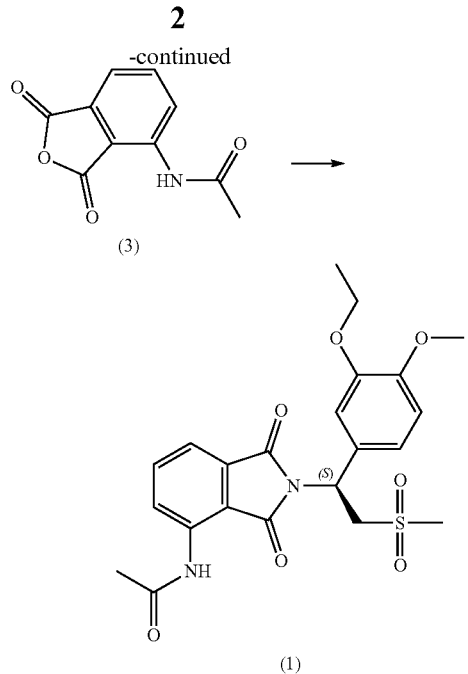

The method prepares apremilast with a low yield, and needs to distill high-boiling acetic acid at the temperature lower than 50° C., and a deacetylated impurity (4) is produced during the reflux reaction and the distillation of acetic acid, which affects the purity of the product. Acetic acid will corrode equipment at high temperatures. Distillation of high boiling acetic acid will also increase workshop production time. The acetic acid that has not been distilled needs to consume a large amount of alkaline liquor to be neutralized, increasing three wastes and production costs, which is not conducive to industrial production.

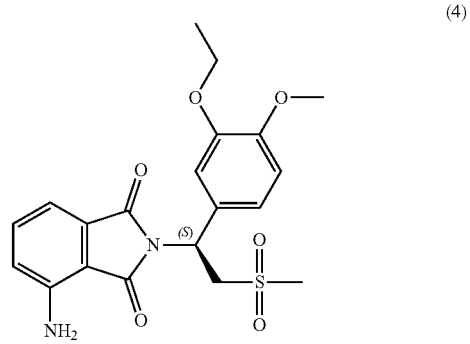

SUMMARY OF THE INVENTION

The object of the present invention is to provide new preparation method for apremilast with high yield and provides a good apremilast purity.

The specific solutions provided by the present invention are as follows:

a preparation method for apremilast represented by formula I, comprising the following methods:

method one: (S)-1-(3-ethoxy-4-methoxyphenyl)-2-(methylsulfonyl)ethylamine N-acetyl-L-leucine salt of formula II is reacted with 3-acetylaminophthalic anhydride of formula III in an aprotic solvent to obtain the compound of formula I;

method two: (S)-1-(3-ethoxy-4-methoxyphenyl)-2-(methylsulfonyl)ethylamine N-acetyl-L-leucine salt of formula II is reacted with 3-acetylaminophthalic anhydride of formula III in an organic solvent in the presence of an organic alkali or an alkali metal hydride to obtain the compound of formula I;

the reaction equation is as follows:

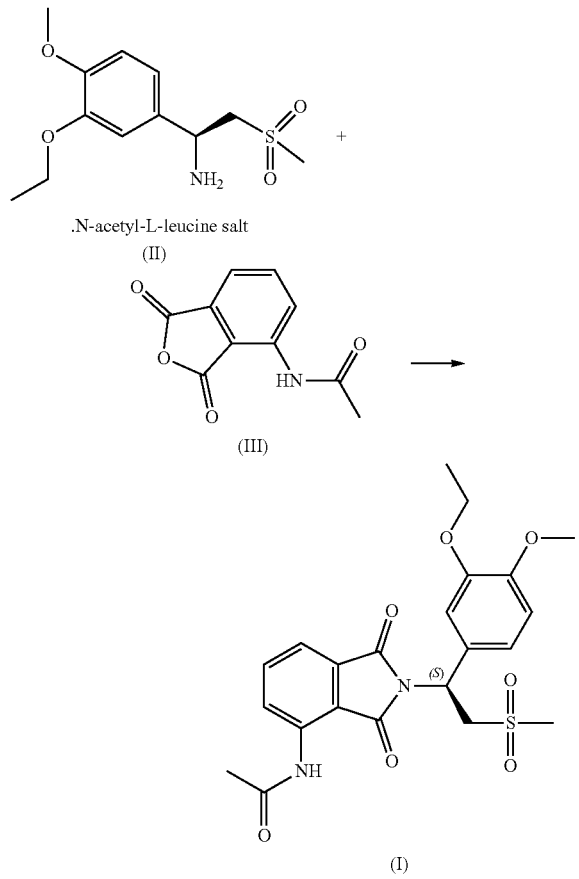

In the solution of the present invention, the aprotic solvent of method one is selected from the group consisting of acetonitrile, tetrahydrofuran, 1,4-dioxane, N,N-dimethylformamide, N,N-dimethylacetamide, N-methylpyrrolidone, toluene, nitrobenzene, 1,2-dichlorobenzene and xylene solvent or any combination thereof; further preferably selected from the group consisting of acetonitrile, toluene, xylene, N,N-dimethylformamide and N-methylpyrrolidone or any combination thereof; most preferably acetonitrile;

wherein the mass to volume ratio of the compound of formula (II) to the aprotic solvent is generally 1 g:(2-20) mL, preferably 1 g:(3-10) mL;

wherein the reaction temperature is controlled within the range of 40° C.-150° C., preferably within the range of 40° C.-90° C., and further preferably 75° C.-80° C.;

wherein the reaction time is generally controlled within the range of 8-24 hours, preferably 12-24 hours, and further preferably 14-22 hours.

In the solution of the present invention, the organic solvent of method two can be selected from the group consisting of a nitrile solvent, an aromatic hydrocarbon, an ester and an aliphatic substituted amide solvent or any combination thereof, and the nitrile solvent is selected from acetonitrile; the aromatic hydrocarbon can be selected from the group consisting of toluene, xylene or a mixture thereof; the ester can be selected from the group consisting of ethyl acetate, isopropyl acetate or a mixture thereof; the aliphatic substituted amide solvent can be selected from the group consisting of N,N-dimethylformamide, N,N-dimethylacetamide or a mixture thereof; preferably selected from the group consisting of acetonitrile, toluene, ethyl acetate, isopropyl acetate and N,N-dimethylformamide or any combination thereof; most preferably selected from the group consisting of acetonitrile, ethyl acetate, toluene and N,N-dimethylformamide or any combination thereof;

wherein the molar ratio of the amount of the compound of formula II to the amount of the organic alkali is generally 1:(0.1-4), and the molar ratio of the amount of the compound of formula II to the amount of the alkali metal hydride is generally 1:(1-3);

wherein the organic alkali is a tertiary amine or a sodium alkoxide, wherein the tertiary amine is selected from the group consisting of triethylamine or trimethylamine, preferably triethylamine; the sodium alkoxide is selected from the group consisting of sodium methoxide or sodium ethoxide, preferably sodium methoxide; the alkali metal hydride is selected from the group consisting of sodium hydride or lithium hydride, preferably sodium hydride.

Wherein the reaction temperature is controlled within the range of 40° C.-120° C., preferably within the range of 40° C.-90° C.;

wherein the reaction time is controlled within the range of 2-24 hours, preferably 12-18 hours;

compared with the prior art, the preparation method provided by the present invention obtains apremilast with high yield, good purity, the method avoids by-products which are relatively easy to be produced in the prior art, and is environmentally friendly and easy to operate. The post-processing of the method is simple, the work efficiency is improved, the production cost is low, and the method is very beneficial to technological production.

EMBODIMENTS

The following examples describe the present invention on a laboratory scale and an industrial scale. The examples exemplify the present invention but are not intended to limit the present invention.

Example 1

10.0 g (0.0224 mol) of (S)-1-(3-ethoxy-4-methoxyphenyl)-2-(methylsulfonyl)ethylamine N-acetyl-L-leucine salt and 4.6 g (0.0224 mol) of 3-acetylaminophthalic anhydride were added to a 250 mL three-necked flask, then 50 mL of acetonitrile was added thereto, and the mixture was heated to 75-80° C., a reaction was carried out with the temperature maintained for 18 hours, then the temperature was cooled to room temperature. The reaction solution was evaporated to dryness, then 60 mL of dichloromethane was added, 25 g of 10% sodium carbonate solution was then added, the obtained mixture was stirred for 10-30 minutes and was layered while standing still, then 25 mL of water was added to the organic layer, the obtained system was stirred for 10-30 minutes and was layered while standing still, the organic layer was evaporated to dryness to obtain a pale yellow solid. 30 mL of absolute ethanol was then added, again, the obtained mixture was evaporated to dryness. Ethanol was used for hot pulping, the obtained product was cooled to 0-5° C. and stirred for 1-2 hours, filtered and drained, and the filter cake was dried under vacuum, then 9.4 g of off-white powders were obtained, yield: 91.2%, HPLC: 99.9%, wherein the HPLC area of the deacetylated impurity (4) was 0.03%.

Example 2

10.0 g (0.0224 mol) of (S)-1-(3-ethoxy-4-methoxyphenyl)-2-(methylsulfonyl)ethylamine N-acetyl-L-leucine salt and 4.6 g (0.0224 mol) of 3-acetylaminophthalic anhydride were added to a 250 mL three-necked flask, then 80 mL of toluene and 10 mL of N,N-dimethylformamide were added thereto, and the mixture was heated to 100° C., a reaction was carried out with the temperature maintained for 12 hours, then the temperature was cooled to room temperature. The reaction solution was evaporated to dryness, then 80 mL of dichloromethane was added, 25 g of 10% sodium carbonate solution was then added, the obtained mixture was stirred for 10-30 minutes and was layered while standing still, 50 mL of water was added to the organic layer, the obtained system was stirred for 10-30 minutes and was layered while standing still, the organic layer was evaporated to dryness to obtain a pale yellow solid. 30 mL of absolute ethanol was then added, again, the obtained mixture was evaporated to dryness. Ethanol was used for hot pulping, the obtained product was cooled to 0-5° C. and stirred for 1-2 hours, filtered and drained, and the filter cake was dried under vacuum, then 9.2 g of off-white powders were obtained, yield: 89.2%, HPLC: 99.9%, wherein the HPLC area of the deacetylated impurity (4) was 0.03%.

Example 3

10.0 g (0.0224 mol) of (S)-1-(3-ethoxy-4-methoxyphenyl)-2-(methylsulfonyl)ethylamine N-acetyl-L-leucine salt and 4.6 g (0.0224 mol) of 3-acetylaminophthalic anhydride were added to (a 250 mL three-necked flask, then 50 mL of ethyl acetate and 1.81 g (0.8 eq) of triethylamine were added thereto, and the mixture was heated to 75-80° C., a reaction was carried out with the temperature maintained for 18 hours. The reaction was stopped, then 100 mL of ethyl acetate was added thereto, and the obtained mixture was cooled to 20-30° C. 30 g of 8% sodium carbonate solution was added to the reaction solution, the obtained mixture was stirred for 10-30 minutes and was layered while standing still, 30 mL of water was added to the organic layer, the obtained system was stirred for 10-30 minutes and was layered while standing still, 30 mL of water was then added to the organic layer, the obtained system was stirred for 10-30 minutes and was layered while standing still, and the organic layer was evaporated to dryness to obtain a pale yellow solid. 30 mL of absolute ethanol was then added, again, the obtained mixture was evaporated to dryness. Ethanol was used for hot pulping, the obtained product was cooled to 0-5° C. and stirred for 1-2 hours, filtered and drained, and the filter cake was dried under vacuum, then 9.8 g of off-white powders were obtained, yield: 95.1%, HPLC: 99.9%, wherein the HPLC area of the deacetylated impurity (4) was 0.04%.

Example 4

10.0 g (0.0224 mol) of (S)-1-(3-ethoxy-4-methoxyphenyl)-2-(methylsulfonyl)ethylamine N-acetyl-L-leucine salt and 4.6 g (0.0224 mol) of 3-acetylaminophthalic anhydride were added to a 250 mL three-necked flask, then 120 mL of isopropyl acetate, 30 mL of acetonitrile and 1.81 g (0.8 eq) of triethylamine were added thereto, and the mixture was heated to 75-80° C., a reaction was carried out with the temperature maintained for 16 hours. The reaction was stopped, and the reaction solution was cooled to 20-30° C. 30 g of 8% sodium carbonate solution was added to the reaction solution, the obtained mixture was stirred for 10-30 minutes and was layered while standing still, 30 mL of water was then added to the organic layer, the obtained system was stirred for 10-30 minutes and was layered while standing still, 30 mL of water was then added to the organic layer, the obtained system was stirred for 10-30 minutes and was layered while standing still, and the organic layer was evaporated to dryness to obtain a pale yellow solid. 30 mL of absolute ethanol was then added, again, the obtained mixture was evaporated to dryness. Ethanol was used for hot pulping, the obtained product was cooled to 0-5° C. and stirred for 1-2 hours, filtered and drained, and the filter cake was dried under vacuum, then 9.6 g of off-white powders were obtained, yield: 93.1%, HPLC: 99.9%, wherein the HPLC area of the deacetylated impurity (4) was 0.03%.

COMPARATIVE EXAMPLE

According to the example of preparing compound A in patent CN 101683334A: 10.0 g (0.0224 mol) of (S)-1-(3-ethoxy-4-methoxyphenyl)-2-(methylsulfonyl)ethylamine N-acetyl-L-leucine salt and 4.6 g (0.0224 mol) of 3-acetylaminophthalic anhydride were added to a 250 mL three-necked flask, then 50 mL of acetic acid was added thereto, and the mixture was heated to 75-80° C., a reaction was carried out with the temperature maintained for 18 hours. The reaction was stopped, the reaction solution was cooled to 40-50° C., and the temperature of the water bath was controlled within the range of 40-50° C. so that the reaction solution was rotarily evaporated until there is no obvious fraction of glacial acetic acid; 150 mL of ethyl acetate was then added thereto, the obtained system was stirred to allow dissolution, and then 100 mL of water was added, the obtained mixture was stirred for 10-30 minutes and was layered while standing still, 100 mL of water was then added to the organic layer, the thus obtained system was stirred for 10-30 minutes and was layered while standing still, 100 g of 8% sodium sodium bicarbonate solution was then added to the organic layer, the thus obtained system was stirred for 10-30 minutes and was layered while standing still. 100 mL of water was then added to the organic layer, the thus obtained system was stirred for 10-30 minutes and was layered while standing still, 100 mL of water was then added to the organic layer, the thus obtained system was stirred for 10-30 minutes and was layered while standing still, and the organic layer was evaporated to dryness to obtain a pale yellow solid. Then 30 mL of absolute ethanol was added, again, the obtained system was evaporated to dryness. 68 mL of absolute ethanol and 34 mL of acetone were added to the solid, the obtained mixture was heated to 60-65° C., stirred to allow complete dissolution, then cooled to 0-5° C. and stirred for 1-2 hours, filtered and drained, the filter cake was dried under vacuum, then 8.6 g of off-white powders were obtained, yield: 83.4%, HPLC: 99.7%, wherein the HPLC area of the deacetylated impurity (4) was 0.22%.

The method for preparing apremilast proposed by the present invention has been described through the examples, and it will be apparent to those skilled in the art that the preparation method of apremilast described herein can be modified or appropriately changed and combined without departing from the content, spirit and scope of the present invention to achieve the technology of the present invention.

It should be noted specifically that all such alternatives and modifications are obvious to those skilled in the art and are considered to be included in the spirit, scope and content of the present invention.

The invention claimed is:

1. A preparation method for apremilast represented by formula I, comprising the following methods:

method one: (S)-1-(3-ethoxy-4-methoxyphenyl)-2-(methylsulfonyl)ethylamine N-acetyl-L-leucine salt of formula II is reacted with 3-acetylaminophthalic anhydride of formula III in an aprotic solvent to obtain the compound of formula I, wherein the aprotic solvent is selected from the group consisting of acetonitrile, tetrahydrofuran, 1,4-dioxane, N,N-dimethylformamide, N,N-dimethylacetamide, N-methylpyrrolidone, toluene, nitrobenzene, 1,2-dichlorobenzene and xylene or any combinations thereof;

method two: (S)-1-(3-ethoxy-4-methoxyphenyl)-2-(methylsulfonyl)ethylamine N-acetyl-L-leucine salt of formula II is reacted with 3-acetylaminophthalic anhydride of formula III in an organic solvent in the presence of an organic alkali or an alkali metal hydride to obtain the compound of formula I, wherein the organic solvent is selected from the group consisting of acetonitrile, toluene, xylene, ethyl acetate, isopropyl acetate, N,N-dimethylformamide, N,N-dimethylacetamide or a mixture thereof;

wherein the reaction equation is as follows:

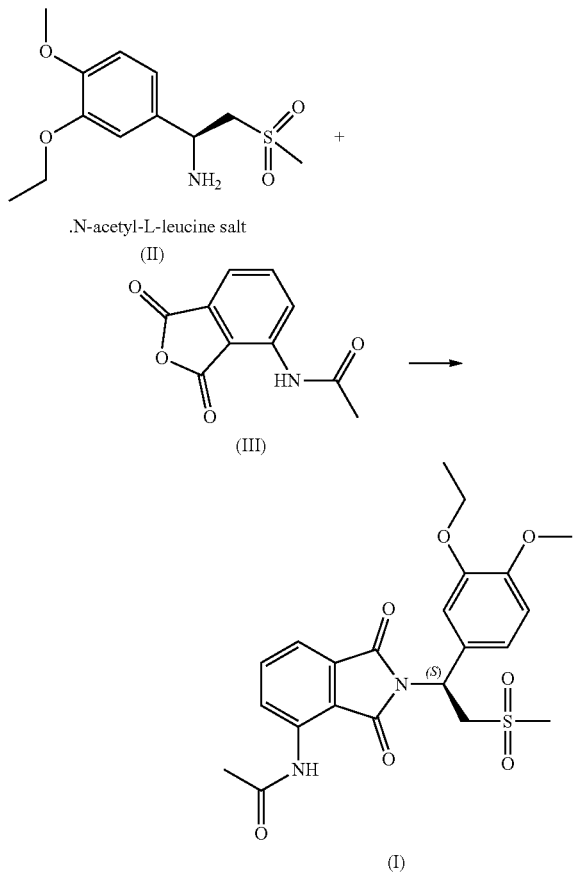

2. The preparation method according to claim 1, wherein the aprotic solvent of the method one is selected from the group consisting of acetonitrile, toluene, xylene, N,N-dimethylformamide and N-methylpyrrolidone or any combinations thereof.

3. The preparation method according to claim 1, wherein for the method one, the mass to volume ratio of the compound of formula II to the aprotic solvent is 1:(3-10) g/mL.

4. The preparation method according to claim 1, wherein the reaction of the method one is carried out within the temperature range of 40° C.-150° C.

5. The preparation method according to claim 1, wherein the reaction time of the method one is controlled within the range of 12-24 hours.

6. The preparation method according to claim 1, wherein the organic solvent of the method two is selected from the group consisting of acetonitrile, ethyl acetate, toluene, isopropyl acetate and N,N-dimethylformamide or any combinations thereof.

7. The preparation method according to claim 1, wherein the organic alkali of the method two is selected from the group consisting of triethylamine, sodium methoxide and sodium hydride.

8. The preparation method according to claim 1, wherein for the method two, the molar ratio of the amount of the compound of formula II to the amount of the organic alkali is 1:(0.1-4), and the molar ratio of the amount of the compound of formula II to the amount of the alkali metal hydride is 1:(1-3).

9. The preparation method according to claim 1, wherein the reaction of the method two is carried out within the temperature range of 40° C.-120° C.; the reaction time being controlled within the range of 2-24 hours.

10. The preparation method according to claim 2, wherein the aprotic solvent of the method one is selected from the group consisting of acetonitrile.

11. The preparation according to claim 4, wherein the reaction of the method one is carried out within the temperature range of 75° C.-80° C.

12. The preparation method according to claim 6, wherein the organic solvent of the method two is selected from the group consisting of acetonitrile, ethyl acetate, toluene and N,N-dimethylformamide or any combinations thereof.

13. The preparation method according to claim 9, wherein the reaction of the method two is carried out within the temperature range of 40° C.-90° C.; the reaction time being controlled within the range of 12-18 hours.

* * * * *